United States Patent
Fuchiwaki et al.

(10) Patent No.: US 9,744,534 B2
(45) Date of Patent: Aug. 29, 2017

(54) ASSAY DEVICE USING POROUS MEDIUM

(71) Applicant: NATIONAL INSTITUTE OF ADVANCED INDUSTRIAL SCIENCE & TECHNOLOGY, Tokyo (JP)

(72) Inventors: Yusuke Fuchiwaki, Takamatsu (JP); Toshihiko Ooie, Takamatsu (JP); Masatoshi Kataoka, Takamatsu (JP); Hiroki Takaoka, Takamatsu (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 17 days.

(21) Appl. No.: 14/432,058

(22) PCT Filed: Sep. 27, 2013

(86) PCT No.: PCT/JP2013/076221
§ 371 (c)(1),
(2) Date: Mar. 27, 2015

(87) PCT Pub. No.: WO2014/051033
PCT Pub. Date: Apr. 3, 2014

(65) Prior Publication Data
US 2015/0266023 A1    Sep. 24, 2015

(30) Foreign Application Priority Data
Sep. 28, 2012   (JP) .................................. 2012-216840

(51) Int. Cl.
*G01N 21/75*    (2006.01)
*G01N 33/52*    (2006.01)
(Continued)

(52) U.S. Cl.
CPC ..... *B01L 3/502769* (2013.01); *B01L 3/50273* (2013.01); *C12Q 1/54* (2013.01);
(Continued)

(58) Field of Classification Search
USPC ......................................................... 422/412
See application file for complete search history.

(56) References Cited

U.S. PATENT DOCUMENTS 6,296,764 B1 *   10/2001   Guirguis .............. G01N 1/2813
                                                                210/319
7,318,911 B2 *   1/2008    Smith ................... B01L 3/0275
                                                                422/513
(Continued)

FOREIGN PATENT DOCUMENTS

JP    2002-357616 A    12/2002
JP    2004-163104 A    6/2004
(Continued)

OTHER PUBLICATIONS

International Search Report dated Nov. 5, 2013, issued in corresponding application No. PCT/JP2013/076221.

*Primary Examiner* — Jill Warden
*Assistant Examiner* — Brittany Fisher
(74) *Attorney, Agent, or Firm* — Westerman, Hattori, Daniels & Adrian, LLP

(57) ABSTRACT

The assay device (10) comprises a micro flow path (76); a porous medium provided near the distal end portion (80) of the micro flow path (76); and a space (82) provided between the micro flow path (76) and the porous medium for controlling the flow rate of a fluid moving from the micro flow path (76) to the space (82). After a fluid moved along the micro flow path (76) based on a lateral flow is brought into contact with the porous medium beyond the space (82) and is absorbed to the porous medium, the fluid is divided by the space (82) so that the fluid stays in the micro flow path (76).

(Continued)

With this structure, it is possible to perform solution exchange in the micro flow path without using an external device such as a pump.

16 Claims, 10 Drawing Sheets

(51) Int. Cl.
  *B01L 3/00* (2006.01)
  *G01N 33/558* (2006.01)
  *C12Q 1/54* (2006.01)
  *G01N 33/543* (2006.01)
  *G01N 31/22* (2006.01)

(52) U.S. Cl.
  CPC ..... *G01N 33/521* (2013.01); *G01N 33/54366* (2013.01); *G01N 33/558* (2013.01); *B01L 2200/16* (2013.01); *B01L 2300/069* (2013.01); *B01L 2300/0809* (2013.01); *B01L 2400/0406* (2013.01)

(56) References Cited

U.S. PATENT DOCUMENTS

| | | | |
|---|---|---|---|
| 2002/0195463 A1 | 12/2002 | Seki et al. | |
| 2003/0077204 A1 | 4/2003 | Seki et al. | |
| 2007/0106198 A1* | 5/2007 | Folden | A61M 1/3627 604/6.14 |
| 2009/0208920 A1* | 8/2009 | Ohman | B01L 3/502746 435/2 |
| 2011/0115905 A1* | 5/2011 | Beumer | G01N 35/1016 348/135 |

FOREIGN PATENT DOCUMENTS

| | | |
|---|---|---|
| JP | 2008-514966 A | 5/2008 |
| JP | 2009-31102 A | 2/2009 |
| JP | 2009-162558 A | 7/2009 |
| JP | 2009-264879 A | 11/2009 |
| JP | 2010-515877 A | 5/2010 |
| JP | 2012-98237 A | 5/2012 |
| WO | 2006/039542 A1 | 4/2006 |
| WO | 2008/049083 A2 | 4/2008 |
| WO | 2008/049083 A3 | 4/2008 |
| WO | 2009/110089 A1 | 9/2009 |

* cited by examiner

Fig. 2
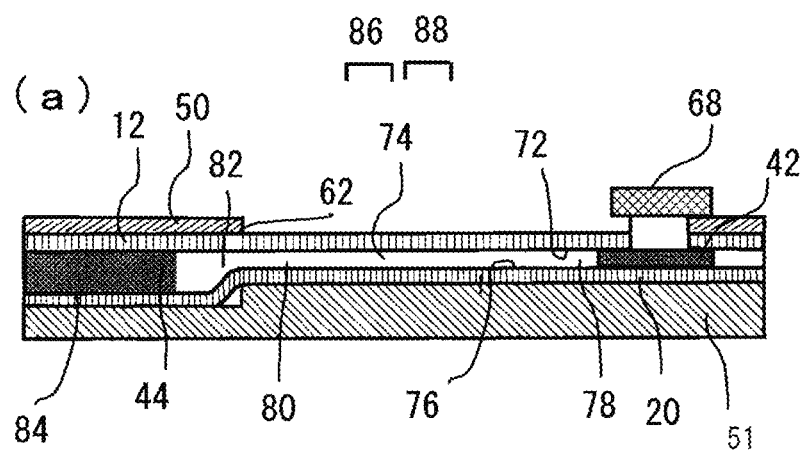
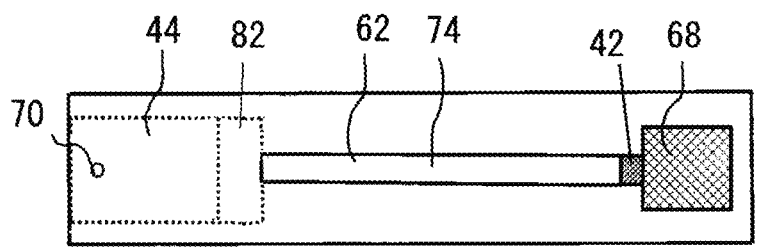

Fig. 9
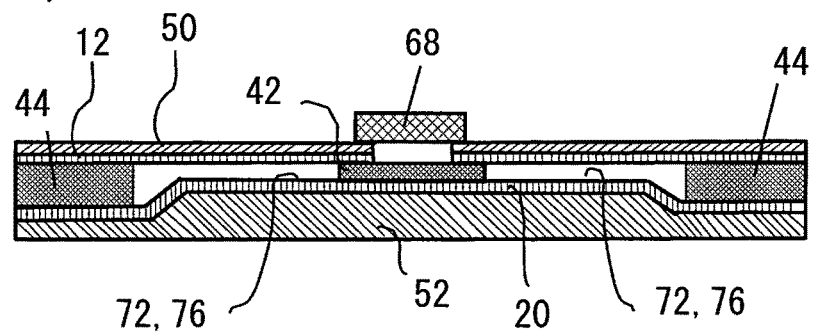
(a)
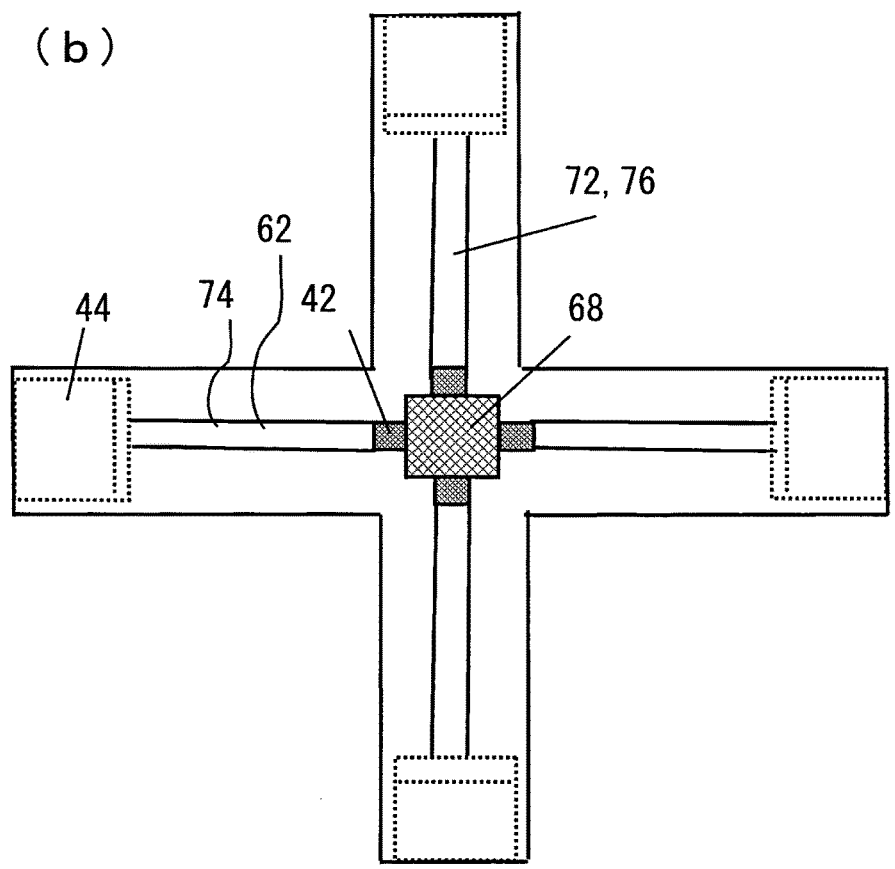
(b)

ASSAY DEVICE USING POROUS MEDIUM

TECHNICAL FIELD

The present invention relates to an assay device, more specifically to a microfluid device having a porous medium.

BACKGROUND ART

Production of microfluid devices for performing biological and chemical screening with a small amount of liquid usually requires expensive semiconductor manufacturing equipment and also requires cumbersome operation and external devices such as a pump. Therefore, practical application of these devices is hampered by problems with costs, durability, and ease of use. In contrast, lateral flow or flow-through paper assay devices are produced by using porous media, and these devices determine the presence or absence of the target substance according to the movement of the substance in the porous medium due to capillary phenomenon; thus, these devices do not require cumbersome operation or external devices such as a pump, and therefore the above drawbacks can be overcome. Accordingly, these devices are attracting attention as enabling point-of-care testing (POCT) during medical diagnosis, and in environments requiring cost reduction, such as in developing countries.

Devices disclosed thus far include a sharp and highly sensitive lateral flow assay (Patent Document 1) in which a control line for preventing diffusion of a solution containing a biomaterial is formed in advance from a casein solution or the like, thereby preventing bleeding on the chromatographic strip, a method of sensitizing color development in immunochromatographic analysis using resonance plasmon effects between the labeled substances such as antibodies (Patent Document 2), a method of forming a fluid-impervious barrier inside a porous hydrophilic medium using polymerization photoresist or a curable polymer, thereby providing a complicated flow path pattern and reaction (Patent Document 3), and a dipstick method in which a solution is developed into multiple flow paths arranged in parallel (Patent Document 4).

CITATION LIST

Patent Literature

Patent Document 1: JP2009-264879A
Patent Document 2: JP2009-162558A
Patent Document 3: JP2010-515877A
Patent Document 4: JP2012-98237A

SUMMARY OF INVENTION

Technical Problem

Although the invention of Patent Document 1 achieves high sensitivity by preventing bleeding on the porous medium and localizing the band by using a control line made of a casein solution or the like, this improvement is limited to cases of significant effects of bleeding on the conventional porous medium. Thus, this method cannot achieve versatile and secure increase in sensitivity and accuracy.

Although Patent Document 2 achieves sensitization in color development and luminescence using resonance plasmon effects between the labeled substances, it is difficult to accurately control the distance between the labeled substances on the porous medium for immunochromatography made of paper or the like; thus, it is not possible to achieve increased sensitization for every single assay with sufficient reproducibility.

Although the invention of Patent Document 3 accomplishes integration of complicated flow paths on the porous medium by using patterning and lamination of the porous medium, the production of such a system requires complicated and costly operation such as polymerization photoresist. Further, Patent Document 3 does not mention a method for increasing sensitivity.

Although the dipstick method of Patent Document 4 is simple, the method requires a large sample amount (e.g., at least several ml) for the measurement. However, in many cases it is difficult to obtain such a large sample amount from, for example, infants or young children.

In the first place, most paper assay devices make the analyte move in a hydrophilic porous medium, and perform reaction, color change, luminescence, etc., on the porous medium. Therefore, these devices have drawbacks including low sensitivity and high variation compared with glass or plastic devices made of a transparent substrate with a hard micro-space, and they are not suited to quantitative analysis. Moreover, since it is extremely difficult to continuously supply flows of multiple liquids and stop the flows in the fluid path on the same hydrophilic porous medium, it is difficult to perform multistage assay; thus, the assays in these devices are almost all limited to a single-step assay.

Accordingly, an object of the present invention is to provide a versatile assay device that has a porous medium and ensures high sensitivity and high accuracy.

Another object of the present invention is to provide an assay device capable of multistage assay.

Solution to Problem

The inventors of the present invention carried out extensive research to attain the above objectives, and conceived of forming a flow path space for liquid samples where no porous medium is present by using two fluid-impervious members and an interposing member to be disposed between them, and providing an assay region in this space. With this structure, the inventors completed the present invention.

Specifically, the present invention is as follows.

Item 1. An assay device comprising:
a micro flow path having a distal end portion;
a porous medium provided near the distal end portion of the micro flow path; and
a space provided between the micro flow path and the porous medium,
wherein, after a fluid moved along the micro flow path based on a lateral flow is brought into contact with the porous medium beyond the space and is absorbed to the porous medium, the fluid is divided by the space so that the fluid stays in the micro flow path.

Item 2. The assay device according to Item 1, wherein the cross-sectional area of the space is greater than the cross-sectional area of the micro flow path.

Item 3. The assay device according to Item 1, wherein the volume of the space is not less than 0.001 µl and not more than 10,000 µl, and the capacity ratio of the space to the micro flow path is not less than 0.01.

Item 4. The assay device according to Item 1, wherein the fluid comprises a first liquid and a second liquid; the first liquid moved from the micro flow path into the space is divided by the space, and one flow stays inside the micro flow path while the other is absorbed to the porous medium;

and then, the second liquid moved into the micro flow path pushes the first liquid staying in the micro flow path to the porous medium, thereby exchanging the first liquid for the second liquid.

Item 5. The assay device according to any one of Items 1 to 4, wherein the assay device is either structured such that:

(i) the width of the space is greater than the width of the micro flow path, the height of the space is equal to or greater than the height of the micro flow path, and the ratio of the distance between the micro flow path and the porous medium to the width of the micro flow path is 0.5 to 5; or (ii) the width of the micro flow path is equal to the width of the space, the height of the space is greater than the height of the micro flow path, and the ratio of the distance between the micro flow path and the porous medium to the width of the micro flow path is 0.5 to 5; or (iii) in a plan view, the space is configured to be enlarged in a tapered shape from the distal end portion of the micro flow path in both directions of the width-wise direction so that the space is connected to the space for storing the absorbent paper at the end of the taper, and the ratio of the distance between the micro flow path and the absorbent paper to the width of the micro flow path is 1 to 5; or (iv) in a plan view, the space is configured with its sides enlarged in a substantially arc-like tapered shape from the distal end portion of the micro flow path in both directions of the width-wise direction so that the space is connected to the space for storing the absorbent paper at the end of the taper, and the ratio of the distance between the micro flow path and the absorbent paper to the width of the micro flow path is 1 to 5; or (v) in a plan view, the space has a first portion that extends from the distal end portion of the micro flow path and is curved toward a longitudinal axis that passes through the width-wise center of the micro flow path, and a second portion that is, in contrast to the first portion, curved toward the outside of the assay device via an inflexion point and is connected to the space for storing the absorbent paper; the width of the lateral sides of the space is enlarged from the distal end portion of the micro flow path toward the space for storing the absorbent paper, and the ratio of the distance between the micro flow path and the absorbent paper to the width of the micro flow path is 1 to 5.

Item 6. The assay device according to Item 1, further comprising a second porous medium in a fluid introduction portion of the micro flow path.

Item 7. The assay device according to Item 6, further comprising plasma separation paper above the second porous medium.

Item 8. The assay device according to Item 6, wherein the micro flow path and the space are treated to be hydrophilic, and the first porous medium and the second porous medium are hydrophilic.

Item 9. The assay device according to Item 1, wherein the micro flow path, the space, the first porous medium, and the second porous medium are held between a pair of fluid-impervious members.

Item 10. The assay device according to Item 9, wherein each surface of the fluid-impervious members that constitute the micro flow path is made of a transparent sheet or film.

Item 11. The assay device according to Item 1, further comprising an assay reagent in the micro flow path between and the space.

Advantageous Effects of Invention

The present invention enables versatile and secure increase in sensitivity and accuracy in the measurement of analyte in a sample with an assay device having a porous medium. The present invention also enables quantitative analysis of the analyte. The present invention further enables continuous supply and cessation of multiple liquids in the same fluid path, thereby enabling multistage assay.

BRIEF DESCRIPTION OF DRAWINGS

FIGS. 2(a) and 2(b) are a schematic cross-sectional view and a schematic plan view of the microfluid device of FIG. 1, respectively.

FIGS. 9 (a) and 9(b) respectively show a schematic cross-sectional view and a schematic plan view of another embodiment of a microfluid device of the present invention having four linear flow paths and four assay regions.

DESCRIPTION OF EMBODIMENTS

Figure 3:
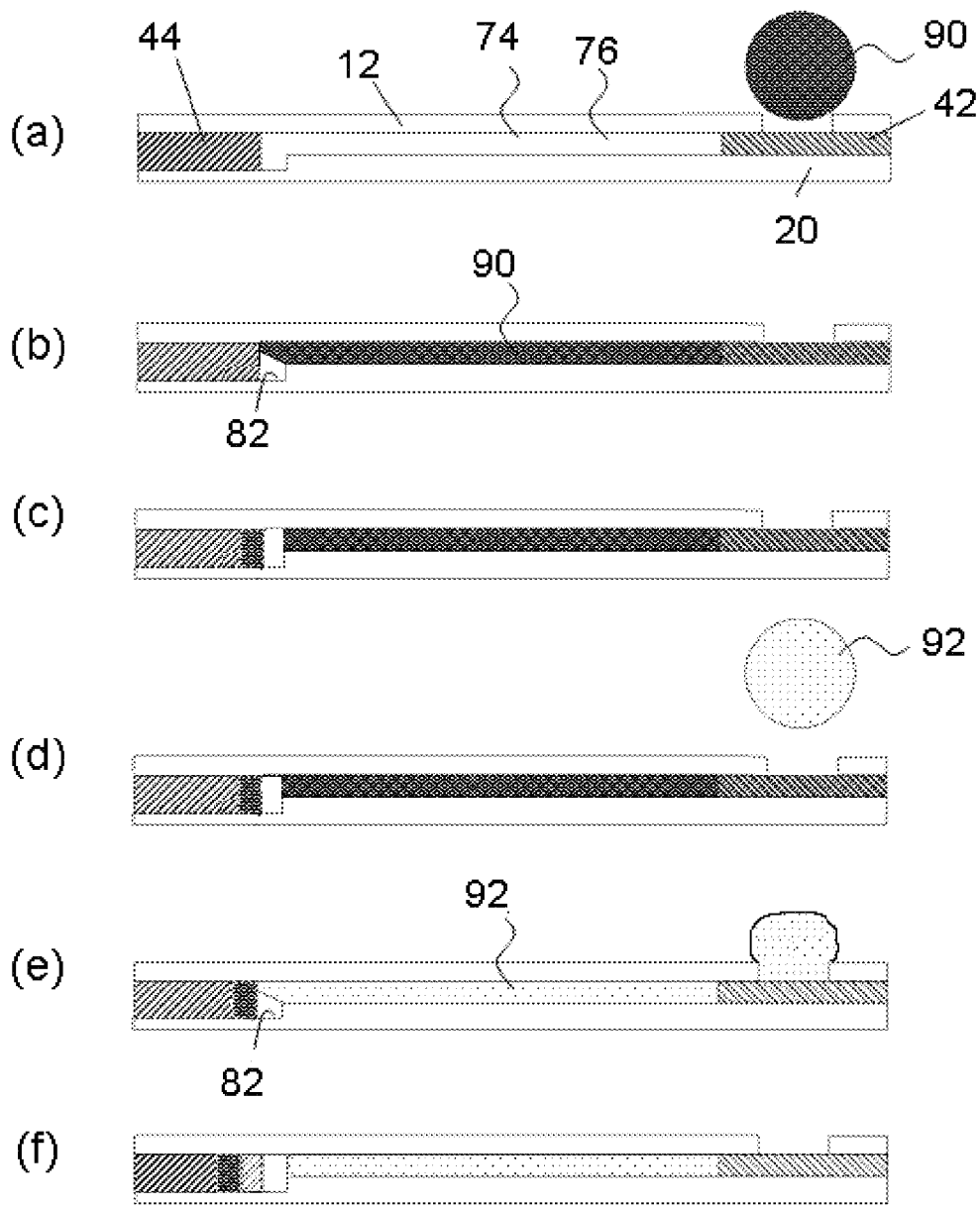
FIGS. 3(a) to 3(f) are schematic diagrams showing the principle of solution exchange when two different solutions are supplied.

The first embodiment of the assay device of the present invention is described below by referring to FIGS. 1 to 3. In the present specification, the positions "upper," "lower," "right," and "left" are based on the orientation of the drawings.

In the present specification, "lateral flow" is a fluid flow made by the force of gravity settling. "Fluid movement based on a lateral flow" means that the driving force of gravity settling is dominant in the movement of a fluid. "Fluid movement based on a lateral flow" is different from fluid movement due to the capillary phenomenon in which the interfacial tension is dominant.

In the present specification, "microfluid device" is a device that performs chemical or biochemical reaction in the channel, and performs detection or measurement on a µl order, specifically, detection or measurement of analytes in a fluid of not less than 1 µl and less than 1,000 µl.

In the present specification, "micro flow path" is a flow path space of a microfluid device that performs detection or measurement on a µl order, specifically, detection or measurement of analytes in a fluid of not less than 1 µl and less than 1,000 µl.

In the present specification, "liquid sample" is not only a chemically pure liquid sample, but also a liquid sample in which gas, another liquid, or solid is dissolved, dispersed, or suspended.

In the present specification, "analyte" is a compound or a composition to be detected or measured from a liquid sample. Examples of analytes include sugars (e.g., glucose), proteins or peptides (e.g., serum proteins, hormones, enzymes, immunoregulatory factors, lymphokines, monokines, cytokines, glycoproteins, vaccine antigens, antibodies, growth factors, or proliferative factors, fats, amino acids, nucleic acids, steroids, vitamins, pathogens and antigens of those pathogens, natural or synthetic chemical substances, contaminants, therapeutic or illegal drugs, and metabolites and antibodies of these substances.

In the present specification, "plastic" means a substance that is obtained by polymerization or molding using a polymerizable material or a polymer material as an essential ingredient, and that is plasticized when heated to a softening temperature or a higher temperature. Examples of plastic also include polymer alloys obtained by combining two or more polymers.

In the present specification, a "film" is a membrane-shaped article having a thickness of 200 µm or less, and a "sheet" has a higher thickness than a "film".

In the present specification, a state where the fluid-impervious member is "soft" means that the fluid-impervious member has a hardness deformable by the pressure of the liquid sample that is generated as the liquid sample passes through the member.

In the present specification, "disposed at the end" is a state where the object is partially included in the end, and "disposed near the end" is a state where the object is disposed adjacent to the end without having another tangible member between the object and the end, either being in contact with the end or not.

Figure 1:
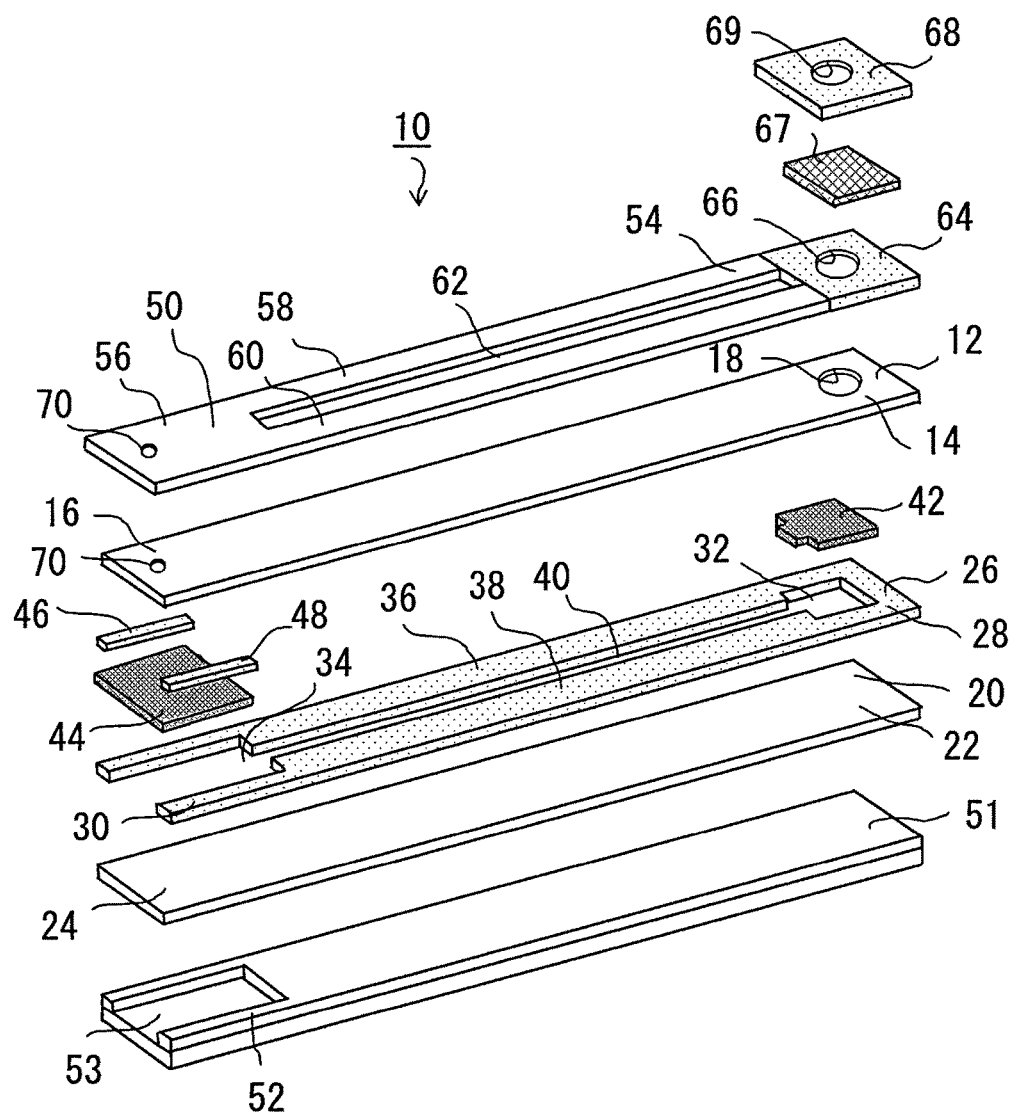
FIG. 1 is a divided perspective view of a microfluid device of the present invention.

FIG. 1 is a divided perspective view of a microfluid device 10, which is an assay device of the present invention. The microfluid device 10 includes a first fluid-impervious member 12 and a second fluid-impervious member 20.

In this embodiment, the first fluid-impervious member 12 and the second fluid-impervious member 20 are substantially rectangular, transparent, and soft sheets or films. The first and the second fluid-impervious members 12 and 20 are made of, for example, plastic, more preferably, plastic having a contact angle of 90 degree or less so as to promote lateral flow (described later) of a hydrophilic liquid sample.

Examples of such a plastic include biodegradable plastics and other polymers, such as polyethylene (PE), polypropylene (PP), polyvinylidene chloride (PVDC), polystyrene (PS), polyethylene terephthalate (PET), polyvinyl chloride (PVC), polyolefin (PO), nylon, polymethylmethacrylate (PMMA), cycloolefin copolymer (COC), cycloolefin polymer (COP), polycarbonate (PC), polydimethylsiloxane (PDMS), polyacrylonitrile (PAN), and polylactic acid (PLA). Examples also include a combination of these substances.

An adhesive tape 26 is disposed as an interposing member between the first fluid-impervious member 12 and the second fluid-impervious member 20. The upper surface and the lower surface of the adhesive tape 26 are adhesive, and the fluid-impervious members 12 and 20 are respectively adhered to the upper and lower surfaces of the adhesive tape 26 so that the fluid-impervious members 12 and 20 are disposed substantially parallel with each other while being also substantially horizontal.

The first fluid-impervious member 12 has a proximal end portion 14 and a distal end portion 16, the adhesive tape 26 has a proximal end portion 28 and a distal end portion 30, and the second fluid-impervious member 20 has a proximal end portion 22 and a distal end portion 24. In the present embodiment, these three members, i.e., 12, 20 and 26, have shapes and sizes that enable them to be stacked on each other by matching their proximal end portions 14, 22, and 28 and their distal end portions 16, 24, and 30.

The proximal end portion 28 of the adhesive tape 26 has an opening 32 in which a second porous medium, in particular, a development paper 42, which serves as a hydrophilic porous medium, is set, and the distal end portion 30 has an opening 34 in which an absorbent paper 44 serving as a first porous medium is set. The openings 32 and 34 are connected via a gap 40 formed between a pair of laterally extending portions 36 and 38. In the present embodiment, the gap 40 has a width narrower than the widths of the openings 32 and 34, and the laterally extending portions 36 and 38 extend along their longitudinal directions while being distantly aligned in a width-wise direction perpendicular to the longitudinal direction. The development paper 42 enables a liquid sample to permeate and develop in the paper. The distal side of the development paper 42 has a projecting portion, which is disposed in the gap 40. The liquid sample that has permeated and developed in the development paper 42 is guided to a micro flow path 76 (described later)(FIG. 2(a)). Further, the absorbent paper 44 for absorbing the developed liquid sample is disposed in the opening 34 while being isolated from the micro flow path 76 via a space 82 (described later)(see FIG. 2(a)).

The material of the development paper 42 and the material of the absorbent paper 44 may be the same or different. For example, the development paper 42 and the absorbent paper 44 are preferably made of a hydrophobic material when the liquid sample is hydrophobic, and they are preferably made of a hydrophilic material when the liquid sample is hydrophilic. When the development paper 42 and the absorbent paper 44 are hydrophilic porous media, they may be selected from, for example, cellulose, nitro cellulose, cellulose acetate, filter paper, tissue paper, toilet paper, paper towel, fabrics, or water-permeable hydrophilic porous polymers.

The development paper 42 is preferably made of a material that does not absorb, or hardly absorbs, the target substance and the assay reagent in the liquid sample. The development paper 42 can be omitted insofar as a structure for enabling the liquid sample to move from an inlet to the micro flow path 76 is provided, and insofar as hydrophilic treatment and hydrophobic treatment were made. This structure is more specifically configured such that, in the structure from the inlet to the micro flow path 76 in the assay device, the space connected to the micro flow path 76 is not completely blocked, thereby allowing the liquid sample to flow.

Further, since a lateral flow in a substantially horizontal direction in the micro flow path 76 mainly affects the flow of the liquid sample toward the micro flow path 76, the difference between the primary lateral pressure before the liquid sample reaches the development paper 42 and the secondary lateral pressure after the liquid sample starts flowing as it passes through the development paper 42 is preferably small. To keep the pressure difference lower than the value at which the lateral flow of the liquid in the micro flow path stops, it is necessary to select an appropriate development paper 42.

Further, the amount of the liquid sample to permeate into the development paper 42 must be less than the total amount of the liquid introduced via the inlet. So as to avoid a decrease in flow rate, the development paper 42 preferably allows only a small amount of a liquid to permeate.

The amount of the liquid sample is generally on a microliter order, specifically, not less than about 1 μl and less than about 1 ml, preferably about 1.5 μl, more preferably not less than about 3.0 μl. By specifying the amount within this range, the detection sensitivity becomes stable, and the detection can thereby be easily performed. The upper limit of the liquid sample is, for example, generally several μl to not more than several hundred μl. Therefore, in many cases, detection is possible even with a drop of a liquid sample. The amount of the liquid sample may be less than the capacity of the micro flow path 76 or the same as the capacity of the micro flow path 76. If the amount of the liquid sample is greater than the capacity of the micro flow path 76, the space 82 (see FIG. 2(*a*) described later) effectively serves as a valve mechanism.

The liquid sample is, in particular, a hydrophilic liquid sample. Examples include biological liquid samples such as human or animal whole blood, blood serum, blood plasma, urine, diluent of feces, saliva, cerebrospinal fluid, or the like. With these samples, it is possible to perform diagnostically useful measurement of analytes in a liquid sample, for example, in a pregnancy test, a urine test, a fecal examination, an adult disease examination, an allergy test, an infectious disease examination, a drug test, a cancer test, or the like. Examples of liquid samples further include food suspensions, drinking water, river water, and soil suspensions. With these liquid samples, it is possible to measure pathogens in food or drinking water, or measure contaminants in river water or soil.

The first fluid-impervious member 12, the adhesive tape 26, and the second fluid-impervious member 20 are connected to each other in a manner such that the development paper 42 is disposed in the opening 32, the absorbent paper 44 is disposed in the opening 34, and, optionally, double-faced adhesive tape 46 and 48 are provided between the absorbent paper 44 and the first fluid-impervious member 12.

As shown in FIG. 2(*a*), the first fluid-impervious member 12, the second fluid-impervious member 20, and the adhesive tape 26 form a flow path 72, which is a path for the liquid sample. Further, the first fluid-impervious member 12, the second fluid-impervious member 20, and the pair of laterally extending portions 36 and 38 form the linear micro flow path 76, and the development paper 42 is disposed to reside in the proximal end portion 78, which serves as a fluid/liquid sample introducing portion, of the micro flow path 76, and near the proximal end portion 78. The distal end portion 80 of the micro flow path 76 is connected to the space 82, and the absorbent paper 44 is disposed in a portion adjacent to the distal end portion 80 of the micro flow path 76, with the space 82 in between.

In the present embodiment, the flow path 72 is formed of, consecutively from right to left, the space of the proximal end portion for storing the development paper 42, the micro flow path 76, the space 82 serving as a valve mechanism, and the space 84 of the distal end portion for storing the absorbent paper 44. When the microfluid device 10 is assembled, the space of the proximal end portion for storing the development paper 42 and the space 84 of the distal end portion for storing the absorbent paper 44 are substantially blocked. In the present embodiment, the volume of the space 82 is greater than that of the micro flow path 76, and the cross-sectional area of the space 82 is greater than the cross-sectional area of the micro flow path 76. The volume of the space 82 is not particularly limited; however, the volume is generally not less than 0.001 μl and not more than 10,000 μl. Further, although the capacity ratio of the space 82 to the micro flow path 76 is also not particularly limited, the capacity ratio is, for example, 0.01 or more.

The space 82 and the micro flow path 76 are preferably subjected to a hydrophilic treatment so as to increase the hydrophilicity of their surfaces in contact with the liquid sample. The hydrophilic treatment includes a treatment using a blocking agent that prevents non-specific adsorption of the specifically-binding substances in the liquid sample to the flow path. Examples of blocking agents include commercially available blocking agents such as Block Ace, bovine serum albumin, casein, skim milk, gelatin, surfactant, polyvinyl alcohol, globulin, blood serum (e.g., fetal bovine serum or normal rabbit serum), ethanol, and MPC polymer. These blocking agents may be used solely or in a combination of two or more.

The height of the micro flow path 76 is, for example, not less than about 15 μm and not more than 1,000 μm (1 mm). The width of the micro flow path 76 is, for example, not less than about 100 μm and not more than about 10,000 μm (1 cm). The length of the micro flow path 76 is, for example, not less than about 10 μm and not more than about 10 cm. The volume of the micro flow path 76 is not less than 0.1 μl and not more than 1,000 μl, preferably not less than 1 μl and less than 500 μl.

An assay region 74 having an assay reagent to be reacted with the analyte in the liquid sample to provide a detectable effect is provided in the middle of the micro flow path 76. This detectable result may be visually observable (e.g., color change), or may be detectable only by using a spectrometer or other measurement means.

The assay reagent may be a chemical substance that is colored by the reaction with the analyte, such as iron (III) ion or a coloring reagent. An enzyme, an antibody, an epitope, or any other substance that can provide a detectable result by being reacted with the analyte may also be used. The assay reagent is fixed to the assay region 74 by using a well-known fixation technique such as physical adsorption methods or chemisorption methods. The assay reagent is preferably fixed to the first fluid-impervious member 12 or the second fluid-impervious member 20, particularly preferably to the first fluid-impervious member 12. Further, the assay reagent may be bonded to an any marker substance, such as radio-isotope, enzyme, coloring molecules such as gold colloid, latex, or the like, colorant, fluorescent material, or a luminescent substance, so as to amplify the detection signal.

When two or more kinds of assay reagents are used, the assay region 74 includes a first assay reagent fixing position 86 and a second assay reagent fixing position 88. The analyte in the liquid sample reacts with the second assay reagent; then, after the composite of the analyte and the second assay reagent is moved, the composite reacts with the first assay reagent. As a result, the composite of the analyte and the second assay reagent further forms a composite with the first assay reagent generally at the first assay reagent fixing position 86. The signal of the resulting composite is detected by using a known method.

When the analyte is an antigen, generally, the first assay reagent is a primary antibody and the second assay reagent is a secondary antibody. The primary antibody and the secondary antibody individually bind to the two different epitopes of the analyte; otherwise, the secondary antibody binds to the epitope of the analyte and the primary antibody binds to the secondary antibody. The primary antibody, the secondary antibody, or both are labeled, and the primary antibody is fixed to the fixed position 86, and the secondary antibody is moved from the fixed position 88 by the flow of the liquid sample. Then, the composite of the antigen, the primary antibody, and the secondary antibody is detected at the fixed position 86. When the analyte is an antibody, the assay reagent contains the antigen, and the signal of the composite produced due to the antigen-antibody reaction is detected in the same manner. When the analyte is an enzyme, the detection or measurement can be performed in the similar manner by using the assay reagent, which serves as the substrate, using the specificity of the enzyme-substrate reaction. When the analyte is a substrate, an enzyme is used as the first assay reagent. The second assay reagent may be optionally used as a coloring reagent.

Optionally, a control region may be provided in the micro flow path 76 in a downstream (distal side) portion of the portion where the assay reagent is supplied. The control region is used to confirm that a sufficient amount of the analyte reaches the assay region. A control reagent is provided in the control region. The control reagent is a reagent that binds to an assay reagent (e.g., the above second assay reagent), which is bonded to the analyte in the liquid sample and is made to flow with the flow of the liquid sample, but does not bind to the analyte. The control reagent may be any molecule or composition well known in the related technical field. The observer can confirm the reliability of the assay result by using, as the control agent, a reagent that causes a color change or the like in response to the reaction with the assay reagent.

Referring back to FIG. 1, a cover member 50 as a first casing for imparting the robustness or rigidity to the microfluid device 10 is provided above the first fluid-impervious member 12. Further, the base member 51 as a second casing for imparting robustness or rigidity to the microfluid device 10 is provided under the second fluid-impervious member 20. The cover member 50 and the base member 51 are respectively connected to the fluid-impervious member 12 and the fluid-impervious member 20 by using the same adhesive tape as the adhesive tape 26, or a similar member.

The cover member 50 has a proximal end portion 54 and a distal end portion 56, and a pair of laterally extending portions 58 and 60 is provided to be closer proximal to the distal end portion 56, along its longitudinal direction. The laterally extending portions 58 and 60 are aligned in the width-wise direction, which is vertical to the longitudinal direction, with a distance between them. Therefore, a slit 62 is formed as a penetrating opening in the major part of the cover member 50 in the longitudinal direction between the pair of laterally extending portions 58 and 60, thereby enabling observation of the assay region 74. Since the slit 62 resides in a position corresponding to the assay region 74, as shown in FIG. 2(b), when the analyte in the liquid sample is analyzed in the microfluid device 10 of the present invention, the observer can visually observe the assay region 74 via the slit 62 and the transparent first fluid-impervious member 12.

A recessed portion 53 for storing the absorbent paper 44 is provided in the distal end portion 52 of the base member 51, thereby keeping the micro flow path 76 horizontal even when the thickness (height) of the absorbent paper 44 is greater than the height of the adhesive sheet 26.

A adhesive tape 64 is disposed proximal to the proximal end portion 54 of the cover member 50. A plasma separation member 67 for separating blood plasma from whole blood is adhered to the adhesive tape 64. Further, another adhesive tape, an adhesive tape 68, is adhered to the plasma separation member 67. The adhesive tape 64 and 68 respectively have circular holes 66 and 69. The circular holes 66 and 69, and the circular hole 18 of the first fluid-impervious member 12 are matched when the microfluid device 10 is assembled. When a liquid sample such as whole blood is supplied to the plasma separation member 67 via the hole 69, the supplied liquid sample passes through the plasma separation member 67 and moves downward, and then reaches the development paper 42 via the hole 66 and the hole 18.

The adhesive tape 64 and 68 are hydrophobic, and thus prevent leakage of the liquid sample from the circular hole 66 to the outside. Since the plasma separation member 67 is caught between the adhesive tape 64 and 68, the plasma separation member 67 is tightly sealed, thereby reducing the drying of the liquid sample permeated into the plasma separation member 67. This reduces volatilization of the liquid sample in the flow path 72. Further, since the adhesive tape 68 is hydrophobic, it is possible to prevent the liquid sample placed in the hole 69 from leaking to the outside of the hole 69, thereby enabling the liquid sample to flow into the development paper 42 with high reproducibility.

Any materials may be used for the cover member 50 and the base member 51; however, the cover member 50 and the base member 51 are preferably made of paper, in particular, cardboard, in terms of cost reduction and easy production of the microfluid device 10. When the analyte is detected based on color change, using a white base member 51 will clarify the color contrast produced by the color change.

As shown in FIGS. 1 and 2(b), an air vent hole 70 is formed on the cover member 50 and on the first fluid-impervious member 12 as a through hole. The air vent hole 70 serves to remove air from the flow path 72 to the outside of the microfluid device 10 when the liquid sample flows from the proximal side to the distal side of the flow path 72 when assay is performed.

Figure 4:
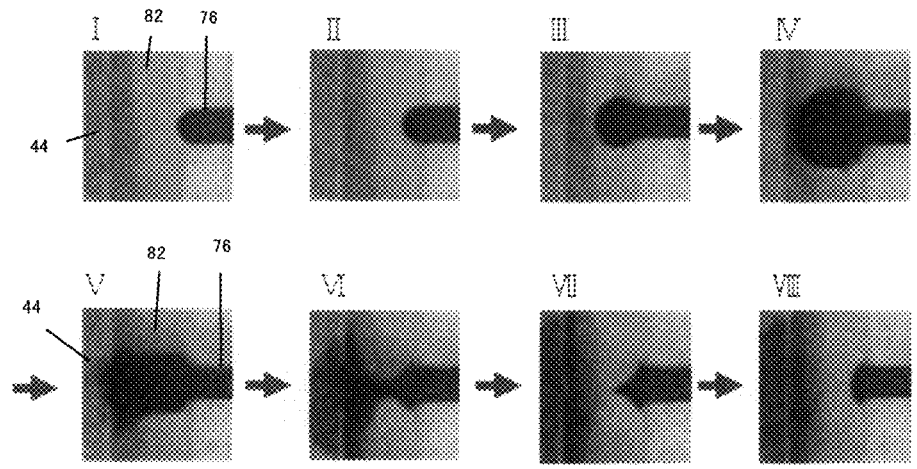
FIG. 4 shows photos of a valve mechanism when blue ink is supplied to the flow path.

The operation of the microfluid device 10 according to the first embodiment of the present invention is described below by referring to FIGS. 3 and 4.

First, the first liquid 90 as a liquid sample is supplied to the inlet of the microfluid device 10 (FIG. 3(a)). As a result, the first liquid 90 permeates into the development paper 42 due to capillarity, and flows into the micro flow path 76 via the distal end of the development paper 42 (FIG. 3(b)).

Without wishing to be bound by theory, the principle of fluid movement in the device of the present invention is assumed to be as follows. When the first fluid-impervious member 12 and the second fluid-impervious member 20, which are soft plastic sheets or films, are oppositely disposed, even though they are partially adhered, they are detached by the lateral flow, and peeling electrification occurs on the surfaces of the fluid-impervious members 12 and 20 facing to each other, thereby attracting the water molecules to the surfaces of the fluid-impervious members 12 and 20. By this attraction of the water molecules and the surface tension of the liquid sample, the first liquid 90 is allowed to flow without greatly decreasing the movement speed.

Further, the flow of the liquid sample that is brought into contact with a porous medium beyond the space 82 is divided into two portions after being absorbed by the porous medium due to the presence of the space 82, which serves as a valve mechanism before the absorbent paper 44 that is provided in a downstream portion. One flow stays in the absorbent paper 44, and the other flow stays inside the micro flow path 76 (FIG. 3(c)). Then, the first liquid 90 stably flows until there is no excess permeated liquid in the development paper 42 (if the device has the plasma separation member 67, until there is no excess liquid in the plasma separation member 67, and if the device does not have the development paper 42, until there is no excess liquid on the upper surface of the inlet); thus, the entire amount of the first liquid 90 is drawn into the micro flow path 76.

Next, the second liquid 92, which is a reagent solution required for the assay, is added to the device dropwise (FIG. 3(d)). The lateral flow is generated again by the second liquid 92, and the second liquid 92 moves in the micro flow path 76 (FIG. 3(e)) so that the entire amount of the second liquid 92 is drawn into the micro flow path 76. The first liquid 90 previously supplied in the micro flow path 76 is pushed to the absorbent paper 44, thereby exchanging the first liquid 90 for the second liquid 92 (FIG. 3(f)). In this figure, the amount of the first liquid 90 is greater than the volume of the micro flow path 76. Substantially the entire volume of the micro flow path 76 is filled with the first liquid 90 in advance.

When the two liquids 90 and 92 are supplied to the microfluid device 10, the space 82 serves to divide the flow of the first liquid 90 into two portions, and keep one portion of the first liquid 90 remaining in the micro flow path 76 to fill substantially the entire volume of the micro flow path 76, and also enables solution exchange of the first liquid 90 for the second liquid. With this structure, the microfluid device 10 enables easy performance of multistage antigen-antibody reaction, such as for ELISA testing.

To ensure the solution exchange, the amount of the second liquid 92 is equal to or greater than the amount of the first liquid 90 with which the micro flow path 76 is filled, although this is not to be limiting. If the amount of the second liquid 92 is less than the amount of the first liquid 90 with which the micro flow path 76 is filled, when the second liquid 92 is supplied to the micro flow path, the first liquid 90, which is kept as a sphere in the distal end portion 80 of the micro flow path 76, and the second liquid 92 cannot be well divided. Even when the sphere of the first liquid 90 is collapsed at the distal end portion 80 and absorbed into the absorbent paper 44, it is not possible to ensure that the solution exchange is completed for the entire amount of the first liquid 90 with which the micro flow path 76 is filled.

As described above, the microfluid device 10 enables a liquid sample to stably flow into a micro flow path without requiring cumbersome operation and external devices such as a pump. Further, the microfluid device 10 also enables solution exchange in the micro flow path.

FIGS. 4I to 4VIII show an experiment for confirming the operation of the valve mechanism of the microfluid device 10 using a blue ink solution. The absorbent paper 44 is disposed distal to the micro flow path, and a blue ink solution is poured in the micro flow path. In this embodiment, the width of the space 82 is greater than the width of the micro flow path 76; preferably, the width of the space 82 is twice or more, more preferably three times or more, than the width of the micro flow path 76. Further, the ratio of the distance between the micro flow path 76 and the absorbent paper 44 to the width of the micro flow path 76 is about 0.5 to about 5, more preferably about 1 to 5. In this example, the height of the bottom surface of the space 82 is the same as the height of the bottom surface of the micro flow path 76. The surface of the top portion of the blue ink solution moved into the space 82 shrinks due to the surface tension exerted in the gas-liquid interface, and therefore is spread into the space 82 generally in the form of a sphere (FIGS. 4I to 4IV). When the top portion of the sphere is brought into contact with the absorbent paper 44, which is a hydrophilic porous medium, the water molecules are absorbed into the absorbent paper 44, and thus the sphere is collapsed (FIG. 4V), thereby dividing the fluid into two portions (FIG. 4VI). As a result, one of the two portions of the fluid is spread into the absorbent pad, and the other stays in the micro flow path (FIG. 4VII). Since the liquid in the micro flow path is in contact with the development paper 42 disposed in the upstream side, the liquid in the flow path will not be absorbed into the absorbent paper 44 in the downstream side (FIG. 4VIII). Therefore, by providing such a valve mechanism that autonomously causes repeated growth and destruction of a sphere of the fluid in the downstream side of the micro flow path, it becomes possible to automatically supply a liquid flow to the micro flow path and statically place the liquid flow in the micro flow path.

In the fluid movement by the capillary force, since the effect of the interfacial tension exerting between the wall of the micro flow path and the liquid is dominant, the fluid is moved as if the liquid is pulled up by its surface tension. During the liquid flow, the top portion of the fluid is concave with respect to the space. Since the surface tension of a liquid has an effect of decreasing the surface area, a force to flatten the concave portion is exerted. Since the top portion of the fluid must become horizontal to obtain the flat state of the fluid, a liquid flow is generated. When a liquid flow is thus generated by a capillary force, the liquid is not in the form of a convex sphere with respect to the space in the distal end of the micro flow path. Therefore, if the capillary force exerted to the fluid is more dominant than the lateral flow, the leakage of the fluid from the distal end does not occur.

Figure 5:
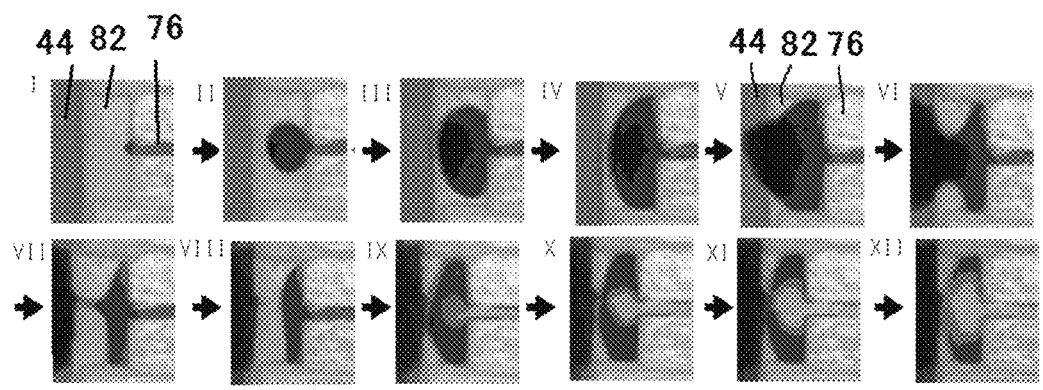
FIG. 5 shows photos of a state where blue ink is supplied to a structure in which the distance between the micro flow path and the absorbent paper is too long relative to the diameter of the micro flow path.

If the blue ink as the first liquid is supplied to the micro flow path 76 having a structure in which the distance between the micro flow path 76 and the absorbent paper 44 is too long relative to the diameter of the micro flow path 76 and therefore the above conditions cannot be satisfied, as shown in FIG. 5, repeated growth and destruction of the sphere of the fluid does not occur, and the fluid stays in the space 82 while being contiguous to the ink in the micro flow path 76 (FIG. 5I-5V). When the amount of the fluid in the space 82 increases, the fluid eventually reaches the absorbent paper 44 (FIGS. 5VI to 5VIII). Then, when the transparent liquid as the second liquid 92 is supplied to the micro flow path 76, the repeated growth and destruction of the sphere of the second liquid 92 also does not occur, and the liquid stays in the space 82 while being contiguous to the ink in the micro flow path 76, thereby being mixed with the first liquid 90 remaining in the space 82 (FIGS. 5IX to 5XII). Thus, the flow of the ink in the micro flow path 76 and the flow of the ink in the space 82 are not separated, and solution exchange fails.

Figure 6:
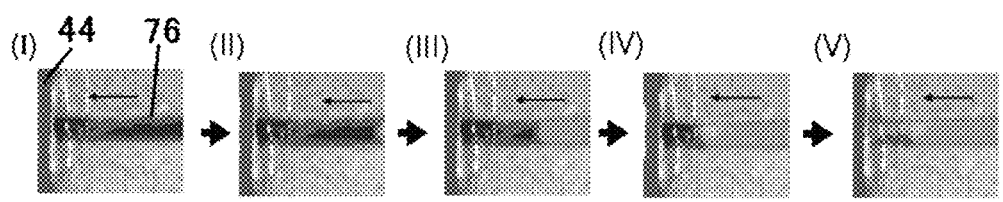
FIG. 6 shows a photo of a state where blue ink is supplied to a structure having no space between the micro flow path and the absorbent paper.

Further, as shown in FIGS. 61 to 6V, if the space 82 is not provided between the micro flow path 76 and the absorbent paper 44, the ink liquid flowing in the direction indicated by the arrow is absorbed to the absorbent paper 44, and the ink is not retained in the micro flow path 76.

The effect of the first embodiment is explained below.

(1) Since the assay region 74 resides in the micro flow path 76, the detection sensitivity greatly increases compared with the previously known immunochromatography or the dipstick test in which an assay region resides in the porous medium. Therefore, it is greatly expected that the problem of false positives and false negatives that occurred frequently in the previously known paper device can be reduced.

(2) Since the micro flow path 76 is a space, the device generally requires only a small amount of liquid sample, compared with previously known immunochromatography or the dipstick test in which the liquid sample moves in a porous medium.

(3) Since high sensitivity and stability are ensured during the measurement, it is possible to perform quantitative analysis of the analyte.

(4) Since the first and second fluid-impervious members 12 and 20 for constituting the micro flow path 76 are made of a soft plastic film or sheet having a contact angle of 90 degree or less, it is possible to move the liquid sample by using an autonomous lateral flow without an external device such as a pump.

(5) Since the first and second fluid-impervious members 12 and 20 are transparent sheets or films, the assay region 74 in the micro flow path 76 can be visually observed.

(6) The capillarity of the absorbent paper 44, the surface tension on the gas-liquid interface of the liquid sample, and the space 82 as a valve mechanism are provided. In particular, the space 82 has a shape and/or a size for enabling the fluid, which has been moved mainly by the lateral flow along the micro flow path 76, to grow into a sphere in the space 82 in the distal end portion 80 and then collapse by the contact with the absorbent paper 44 to be absorbed into the porous medium 44. Therefore, it is possible to autonomously enforce and stop the supply of the liquid sample into the micro flow path. Furthermore, it is possible to continuously and repeatedly supply multiple liquid samples, thereby measuring multiple items.

(7) Since the side wall of the micro flow path 76 is made of the adhesive tape 26, it is possible to easily equalize the height of the micro flow path 76. Further, the micro flow path 76 can be easily constructed at low cost, compared with constructing the micro flow path by thermocompression bonding.

(8) Since the development paper 42, which is a hydrophilic porous medium, is provided in the proximal end portion of the flow path 72, the liquid that has passed the plasma separation member 67 is supplied to the micro flow path 76 via the development paper 42 with high reproducibility, and flows in the path. Generally, the plasma separation using a separation membrane or a micro flow path frequently has problems including discontinuation of the separation due to the aggregation of blood cells or clogging, and contamination by hemolyzed blood or blood cell components because of the strong pressure of a pump. However, by optimizing the above structure, it is possible to cause only the blood plasma components in the whole blood to flow into the micro flow path 76 with high reproducibility by using the plasma separation member 67 and the lateral flow, which is a soft pressure.

(9) Since the holes 18 and 70 for separating the flow path 72 from the external air are respectively blocked with the development paper 42 and the absorbent paper 44, which are wet porous media, the liquid in the flow path 72 is not easily volatilized.

(10) Since the device enables immediate diagnosis of whole blood with the plasma separation member 67, significant improvement in rapid and efficient disease detection and new drug development can be expected.

(11) Since the development paper and/or the porous medium are made of, for example, cellulose, nitro cellulose, cellulose acetate, filter paper, tissue paper, toilet paper, paper towel, fabrics, porous polymer, or the like, the development paper and/or the porous medium may be easily prepared by obtaining inexpensive commercially available paper.

(12) Since the microfluid device 10 can be very easily and inexpensively produced using commercially available inexpensive porous media, transparent film, adhesive tape, paper and the like, the device may be developed for markets that cannot afford such a device, for example, hospitals in developing countries; the device may also be developed for over-the-counter markets in Japan or developed countries. The device thus can help improve quality of life (QOL) of people all over the world.

(13) Since the component members of the microfluid device 10 are all made of soft materials, in particular, since the first and second fluid-impervious members 12 and 20 are made of plastic, the interposing member is made of adhesive tape 26, and the cover member 50 and the base member 51 are made of paper, the device may be cut with scissors or a utility knife, thereby separating the sample from the micro flow path 76. Therefore, the device may also be used as a life science research support tool in the future, such as a tool for gene analysis.

The first embodiment has been described as an example of the present invention; however, the present invention is not limited to the first embodiment, and may be altered in many ways as follows.

At least one of the first fluid-impervious member 12, the second fluid-impervious members 12, and the interposing member may be semitransparent or nontransparent. The first and second fluid-impervious members 12 and 20 and the interposing member may be made of materials other than plastic, such as resin, glass, metal or the like, insofar as they do not allow fluid permeation. Further, the materials of the first and second fluid-impervious members 12 and 20 and the interposing member may be the same or different. If the materials of the first and second fluid-impervious members 12 and 20 and the interposing member are different, only the first fluid-impervious member 12 may be transparent, or only the first fluid-impervious member 12 may be made of a soft sheet or film.

The shapes and the sizes of the hole 18 of the first fluid-impervious member 12 and the hole 66 of the adhesive tape 64 are not particularly limited, insofar as they can communicate with the development paper 42.

In the first embodiment, the height of the bottom surface of the space 82 is lower than the height of the bottom surface of the micro flow path 76. However, the height of the bottom surface of the space 82 may be the same as the height of the bottom surface of the micro flow path 76.

The shape of the space 82 is not limited to that shown in the first embodiment. For example, the shapes shown in the plan views in FIGS. 7(a) to 7(d) and the lateral views in FIGS. 7(e) to 7(h) may be used.

Figure 7:
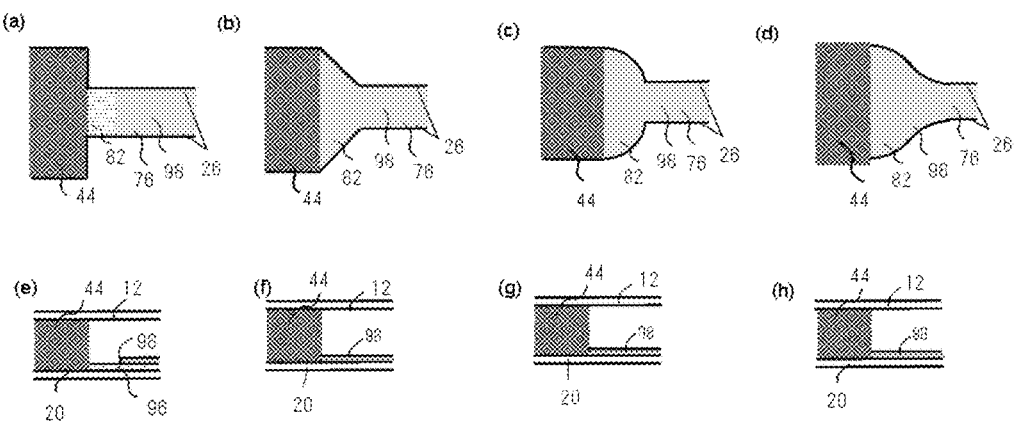
FIG. 7(a) to FIG. 7(d) are plan views showing other examples of the space.
FIG. 7(e) to FIG. 7(h) are lateral views showing embodiments of the spaces of FIG. 7(a) to FIG. 7(d).

In the embodiment shown in FIGS. 7(a) and 7(e), the adhesive tape 96 is provided on the bottom surfaces of the micro flow path 76 and the space 82, and a fluid-impermeable sheet 98, which is made of the same material as that of the second fluid-impervious member 20 or a different material from that of the second fluid-impervious member 20, is provided above the adhesive tape 96; further, a hydrophilic treatment layer made of a blocking agent is formed on the sheet 98. At the portion where the sheet 98 ends, the adhesive tape 96 is exposed, thus providing the space 82. The width of the micro flow path 76 is the same as the width of the space 82, and the space 82 has the first fluid-impervious member 12 as its upper surface, which is also the upper surface of the micro flow path 76. The bottom surface of the space 82 is lower than the bottom surface of the micro flow path 76. More specifically, the height of the space 82 is higher than the height of the micro flow path 76. The ratio (B/A) of distance B between the micro flow path 76 and the absorbent paper 44 as the first porous medium to width A of the micro flow path 76 is preferably 0.5 to 5.

In the embodiment shown in FIGS. 7(b) and 7(f), in a plan view, the space 82 is configured to be enlarged in a tapered shape from the distal end portion of the micro flow path 76 in both directions of the width-wise direction so that the space 82 is connected to the space for storing the absorbent paper 44 at the end of the taper. More specifically, in a plan view, the space 82 corresponds to the trapezoidal portion. In this embodiment, as in the case above, the fluid-impermeable sheet 98, which is made of the same material as that of the second fluid-impervious member 20 or a different material from that of the second fluid-impervious member 20, is provided on the bottom surfaces of the micro flow path 76 and the space 82; further, a hydrophilic treatment layer made of a blocking agent is formed on the sheet 98. The ratio (B/A) of distance B between the micro flow path 76 and the absorbent paper 44 to width A of the micro flow path 76 is preferably 1 to 5.

In the embodiment shown in FIGS. 7(c) and 7(g), in a plan view, the space 82 is configured with its sides enlarged in a substantially arc-like tapered shape (substantially ¼ of a circle) from the distal end of the micro flow path 76 in both directions of the width-wise direction so that the space 82 is connected to the space for storing the absorbent paper 44 at the end of the taper. In this embodiment, as in the case above, the fluid-impermeable sheet 98, which is made of the same material as that of the second fluid-impervious member 20 or a different material from that of the second fluid-impervious member 20, is provided on the bottom surfaces of the micro flow path 76 and the space 82; further, a hydrophilic treatment layer made of a blocking agent is formed on the sheet 98. The ratio (B/A) of distance B between the micro flow path 76 and the absorbent paper 44 to width A of the micro flow path 76 is preferably 1 to 5.

In the embodiment shown in FIGS. 7(d) and 7(h), in a plan view, the space 82 has a first portion that extends from the distal end of the micro flow path 76 and is curved toward the longitudinal axis that passes through the width-wise center of the micro flow path; and a second portion that is, in contrast to the first portion, curved toward the outside of the assay device via the inflexion point and is connected to the space for storing the absorbent paper 44; the width of the lateral sides of the space 82 is enlarged from the distal end of the micro flow path 76 toward the space for storing the absorbent paper 44. In this embodiment, as in the case above, the fluid-impermeable sheet 98, which is made of the same material as that of the second fluid-impervious member 20 or a different material from that of the second fluid-impervious member 20, is provided on the bottom surfaces of the micro flow path 76 and the space 82; further, a hydrophilic treatment layer made of a blocking agent is formed on the sheet 98. The ratio (B/A) of distance B between the micro flow path 76 and the absorbent paper 44 to width A of the micro flow path 76 is preferably 1 to 5.

In the embodiment shown in FIGS. 7(b) and 7(f), the embodiment shown in FIGS. 7(c) and 7(g), and the embodiment shown in FIGS. 7(d) and 7(h), the space 82 has the first fluid-impervious member 12 as its upper surface, which is also the upper surface of the micro flow path 76. The upper surface of the space 82 is thus flush with the upper surface of micro flow path 76. The bottom surface of the space 82 is preferably lower than the bottom surface of the micro flow path 76, and the height of the space 82 is preferably higher than the height of the micro flow path 76; however, the bottom surface of the space 82 and the bottom surface of the micro flow path 76 may also be flush with each other.

Also in the embodiment shown in FIGS. 7(a) to 7(h), the space 82 serves as a valve mechanism, and the solution exchange is effectively performed (data are omitted).

Figure 8:
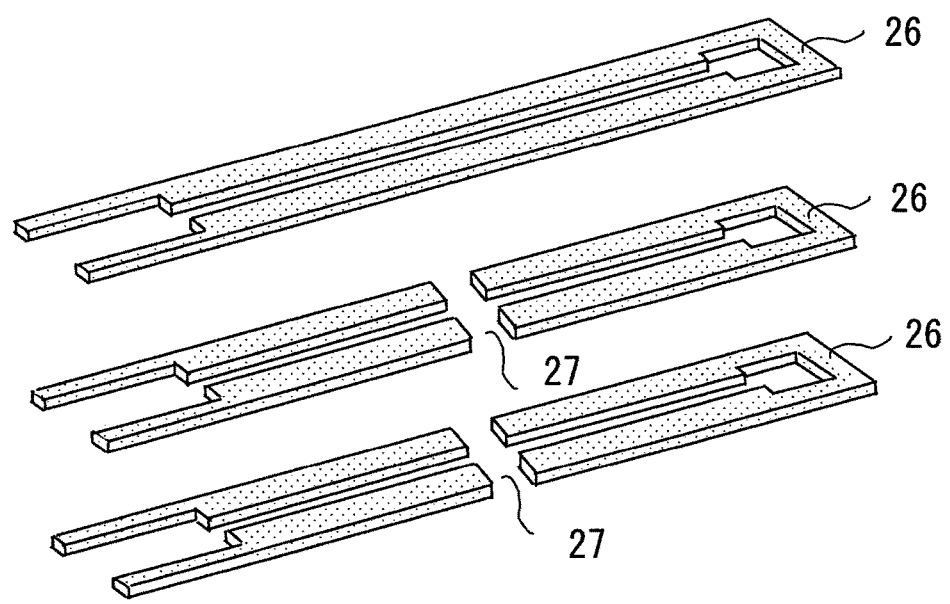
FIG. 8 is a divided perspective view showing another example of interposing members.

It is possible to vertically stack multiple interposing members, such as multiple pieces of adhesive tape 26, on each other so as to adjust the height of the micro flow path 76. Further, the interposing member is not limited to a single member and may be composed of multiple members connected in a horizontal direction so as to avoid leakage of the liquid sample. For example, as shown in FIG. 8, three pieces of adhesive tape 26 may be stacked and bonded together. In this case, the two lower adhesive tape pieces 26 are cut off in the middle of the longitudinal direction, and the micro flow path 76 may be decreased in thickness at this cut-off portion 27 when the three adhesive tape pieces 26 are stacked. By forming the second fluid-impervious member 20 from a soft film such as PVDC, it is possible to cover such a level difference in the flow path according to the shapes of irregularities. By forming a large thickness portion in the flow path, a projection portion that retains the liquid sample in the flow path due to the viscous force can be provided. This increases the force to retain the fluid in the flow path, thereby reducing the influence of volatilization. By decreasing the thickness of the flow path, the reaction space is reduced, and the diffusion (moving) distance and the time for mixing by diffusion can be decreased, thereby greatly reducing the reaction time.

The interposing member is not limited to the adhesive tape 26, and a different member may be used insofar as it hermetically seals the fluid flowing space including the micro flow path 76, the space 82, etc. For example, it is possible to use plastic or a film as the interposing member, and bond it with the fluid-impervious members 12 and 20 by thermocompression bonding or by using an adhesive. They may also be bonded by surface modification by performing surface plasma treatment. Thus, the interposing member is not limited to double-sided tape.

It is also possible to form the distal end portion 30 of the interposing member as a closed end, thereby forming a cyclic interposing member. With this cyclic interposing member the liquid tightness of the assay device can be increased.

The liquid sample is not limited to blood. The assay device is capable of detecting various analytes in various liquid samples.

If the liquid sample is not blood, the adhesive tape 68 and the plasma separation member 67 may be omitted. Instead of the plasma separation member 67, a filter for removing unwanted substances contained in the liquid sample may be provided.

A hydrophilic film may be provided at or near the proximal end portion of the flow path 72, as the second porous medium instead of the development paper 42 or in addition to the development paper 42 so as to impart a hydrophilic property. "Hydrophilic film" refers to a blocking agent for preventing non-specific adsorption of the specifically-binding molecules in the liquid sample to the flow path. Examples of blocking agents include commercially available blocking agents such as Block Ace, bovine serum albumin, casein, skim milk, gelatin, surfactant, polyvinyl alcohol, globulin, blood serum (e.g., fetal bovine serum or normal rabbit serum), ethanol, and MPC polymer. These blocking agents may be used solely or in a combination of two or more.

The position of the slit 62 provided in the cover member 50 corresponds to the position of the assay region 74. The shape and the size of the slit 62 are not particularly limited insofar as the observation of the assay region 74 is possible.

The cover member 50 and/or the base member 51 may be made of a porous medium other than paper, such as plastic, resin, glass, or metal.

The base member 51 may have a slit. For example, when the analyte is detected by way of luminescence or fluorescence measurement, a slit, such as the slit 62 shown in FIG. 1, may be provided in the base member 51, and the measurement may be performed by placing the microfluid device on a mirror surface or a metal flat plate of aluminum and stainless-steel that reflects light, etc.

The recessed portion 53 in the distal end portion 52 of the base member 51 may be omitted when the thickness of the absorbent paper 44 is less than the thickness of the adhesive sheet 26.

If the first fluid-impervious member 12 and/or the second fluid-impervious member 20 has sufficient robustness or rigidity required for the structure of the microfluid device 10 by themselves, the cover member 50 and/or the base member 51 may be omitted.

The first fluid-impervious member 12, the second fluid-impervious member 20, the adhesive tape 26, the cover member 50, and the base member 51 are configured to be matched with each other in shape and size; however, insofar as the micro flow path 76 can be provided, the shapes and the sizes of these members may be suitably changed. For example, it is possible to configure the cover member 50 and the base member 51 to be larger than the other members, and connect the cover member 50 and the base member 51 to each other.

The position of the air vent hole 70 for ventilation of the flow path 72 is not limited insofar as the hole 70 enables the flow path 72 to ventilate in a portion above the absorbent paper 44 or near the portion. The hole 70 may be omitted if the microfluid device 10 is operable without the hole.

The microfluid device 10 may have multiple flow paths. For example, FIGS. 9(a) and 9(b) show a different example in which the microfluid device 10 has four flow paths 72. The four flow paths 72 unite at their proximal ends and are radially arranged so that the angle between adjacent flow paths is substantially vertical. In this case, the liquid sample supplied to the plasma separation member 67 radially flows into the four micro flow paths 76, and the analyte in the liquid sample is analyzed or detected in the assay region 74 of each micro flow path 76. The excess liquid sample is absorbed to the absorbent paper 44. By providing different assay reagents in these assay regions 74, it becomes possible to simultaneously analyze or detect up to four items with one liquid sample.

Figure 10:
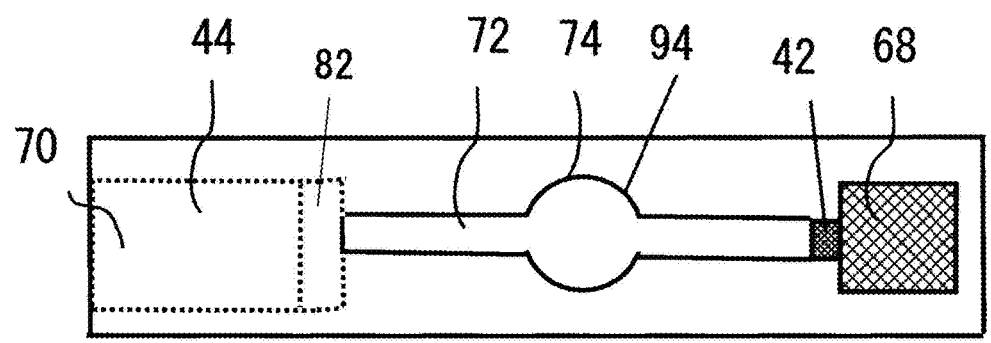
FIG. 10 is a schematic plan view showing another embodiment of the microfluid device of the present invention having a width enlargement portion.

As shown in a different example in FIG. 10, the micro flow path 76 may have a width enlargement portion 94, which has a wider width than that of the micro flow path 76, in the middle of the path. By using the width enlargement portion 94 as the assay region 74, and bonding, for example, an assay reagent such as the primary antibody to the liquid sample, it is possible to react a large amount of antigen and antibody in a region having a short length in terms of the length direction of the micro flow path 76, compared with the case where the micro flow path 76 has a uniform width. Further, by forming the width enlargement portion 94 into a circle or an oval, it is possible to prevent the flow of the liquid sample from accumulating.

The present invention is more specifically explained below in reference to Examples. However, the present invention is not limited to these examples.

The disclosures of all patent applications and documents referred to in this specification are herein incorporated by reference.

EXAMPLES

Example 1

Confirmation of Solution Exchange by Valve Mechanism in Micro Flow Path

5 µl of a buffer solution (0.1 M phosphate buffer; pH of 7.4) and 5 µl of a fluorescence reagent (FITC solution; 10 nM) were alternately supplied to the assay device of the present invention having a space as a valve mechanism, and an optical probe (No. 4040 (spot dia.: 0.4 mm, Nippon Sheet Glass Co. Ltd.) was applied to a portion 1 mm from the distal end of the micro flow path, thereby measuring the fluorescence intensity with an optical fiber fluorescence detector (FLE1100B, Nippon Sheet Glass Co. Ltd.).

Figure 11:
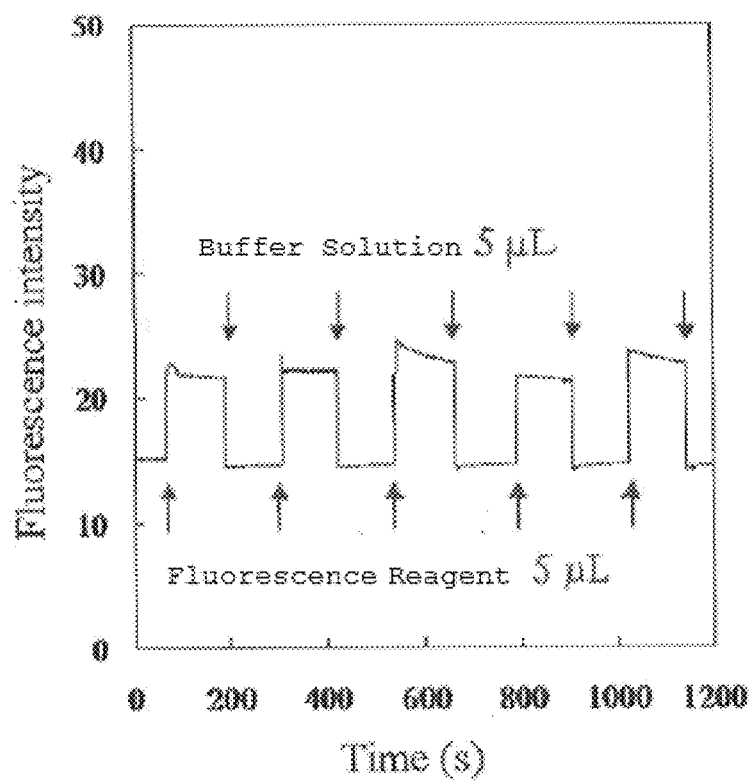
FIG. 11 is a graph showing an example of solution exchange. The horizontal axis denotes time, whereas the vertical axis denotes fluorescence intensity.

As a result, it was confirmed that the buffer solution and the fluorescence reagent alternately flowed in the micro flow path, and that the solution exchange in the micro flow path was thus effectively performed (FIG. 11).

Example 2

Assay Using Antibody

The specification of the assay device of the present invention is as follows.
Micro Flow Path: width=1 mm, length=13 mm
The First Fluid-impervious Member (transparent film obtained from Epson)
Material: PET
Size: 35 mm×12 mm×0.13 mm (length×width×thickness)
The second fluid-impervious member (transparent film obtained from Asahi Kasei)

Material: PVDC
Size: 35 mm×12 mm×0.01 mm (length×width×thickness),
Interposing Member (adhesive tape obtained from Plando Sangyou
Material: A4 adhesive transfer sheet (lamination in which an 25-μm adhesive layer, a 15-μm film layer, and 25-μm an adhesive layer are sequentially stacked)
Cover Member
Material: Progami (cellulose obtained from Aoyagi)
Size: 35 mm×12 mm×0.33 mm (length×width×thickness)
Base Member
A lamination of three pieces of cardboard (each having a thickness of 0.33 mm)
Two of the pieces of cardboard have an opening with the same form as the opening 34, and a space with a thickness of about 0.5 mm for sufficiently storing the absorbent paper 44. The third piece of cardboard does not have a space as the opening 34.
Material: Progami (cellulose obtained from Aoyagi)
Size: 35 mm×12 mm×0.99 mm (length×width×thickness)
Plasma Separation Paper (obtained from Nihon Pall Ltd.)
Size: 5 mm×5 mm (length×width)
Absorbent Paper (obtained from Nippon Paper Crecia Co., Ltd.)
Size: 8 mm×10 mm (length×width)
Whole blood obtained from a human test subject was used as a liquid sample, and adiponectin in the blood was detected.

The interface for identifying the analyte was produced as follows. The first fluid-impervious member 12 made of PET was used. Masking tape (with rubber-based adhesive) was placed in the first fluid-impervious member 12 in a portion where an antibody was to be fixed. A 4% Block Ace solution (phosphate buffer; pH of 7.4) was applied to the portion, and dried by being left unattended for 1 hour. Thereafter, the masking tape was peeled off. The detection of adiponectin, which is the analyte, in the blood was performed using a human adiponectin ELISA kit (96 assay, CY-8050; CycLex Co., Ltd.). The antibody and the antigen were prepared according to a method recommended for the kit. More specifically, 1% of trehalose was mixed with a primary antibody solution prepared by the method recommended for the kit, and a 1 μl droplet of the liquid was placed in the portion from which the masking tape has been removed. The sample was left unattended for an hour, thereby fixing the primary antibody to the first fluid-impervious member 12. The amount of the antibody and the concentration of the trehalose vary depending on the type of the antibody and the size of the micro flow path 76.

The chemical luminescence intensity was measured for an Example in which the interface was prepared by fixing the primary antibody by physisorption to a circular region having a diameter of 1 mm of the first fluid-impervious member 12 in the assay region 74 of the assay device of the present invention, and for a Comparative Example in which nitro cellulose paper was placed in the circular region with a diameter of 1 mm. A Protran nitrocellulose transfer membrane (Whatman) was used as the nitro cellulose paper.

The solution exchange was performed in the following order. First, the device was washed with 10 μl of a physiological saline solution, reacted with 10 μl of 20-ng/ml antigen for 10 minutes, washed with 10 μl of a physiological saline solution, reacted with 10 it of 200-fold diluted HRP-labeled secondary antibody solution for 10 minutes, washed with 10 μl of a physiological saline solution, and then reacted with 5 μl of SuperSignal West Femto (Thermo Scientific) luminescence substrate solution for 30 minutes. An ImageQuant LAS4000/4010 (GE Healthcare) was used as the measurement device.

Figure 12:
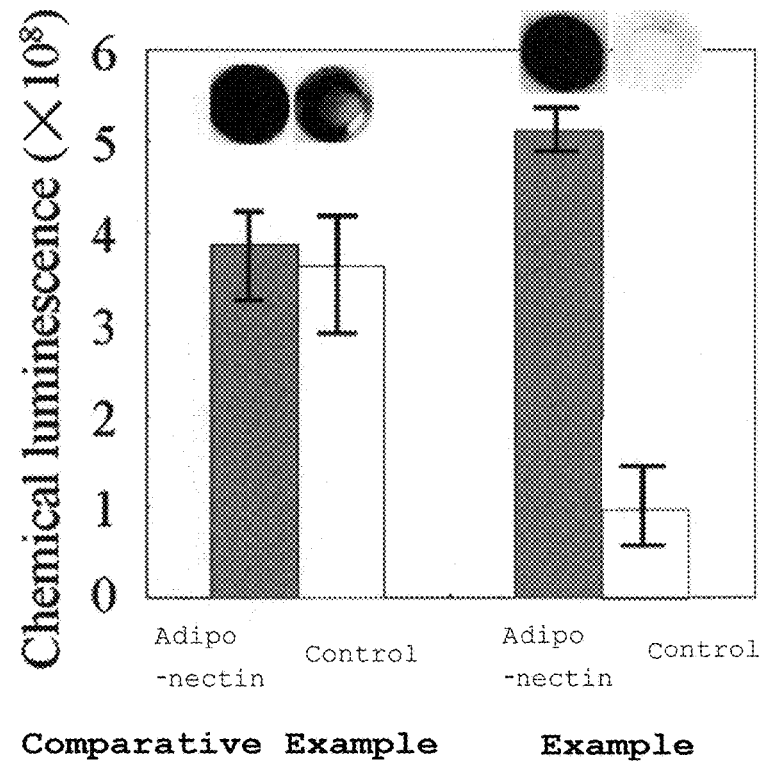
FIG. 12 is a graph showing results of an assay as a comparison between a paper device of the Comparative Example and a device of the present invention. The device on the left is a device of the Comparative Example in which nitro cellulose paper is disposed in the assay region, and the device on the right is the device of the present invention. The dark bar denotes a case using 20 ng/ml (10 mL) adiponectin as a analyte, and the white bar denotes a control using no analyte. The vertical axis denotes the chemical luminescence intensity.

The results confirmed that the luminescence value of the liquid sample in the assay device of the present invention was greater than in the Comparative Example, that the difference between the case where the antibody was fixed and the control with regard to the antibody response with the liquid sample was clear, and that the detection sensitivity thus greatly increased (FIG. 12).

Example 3

Improved Method of Example 2

In the method of Example 2, after the primary antibody was fixed by physisorption to the first fluid-impervious member 12, 3% trehalose was mixed with the secondary antibody solution prepared by the method recommended for the kit, and the mixture was applied on Block Ace placed upstream of (proximal to) the portion where the primary antibody was fixed, and left unattended for an hour, thereby fixing the secondary antibody to the first fluid-impervious member 12.

Next, reaction with 3 μl of 50-ng/ml antigen for 10 minutes and reaction with 5 μl of SuperSignal West Femto (Thermo Scientific) luminescence substrate solution for 30 minutes were performed. An ImageQuant LAS4000/4010 (GE Healthcare) was used as the measurement device.

Figure 13:
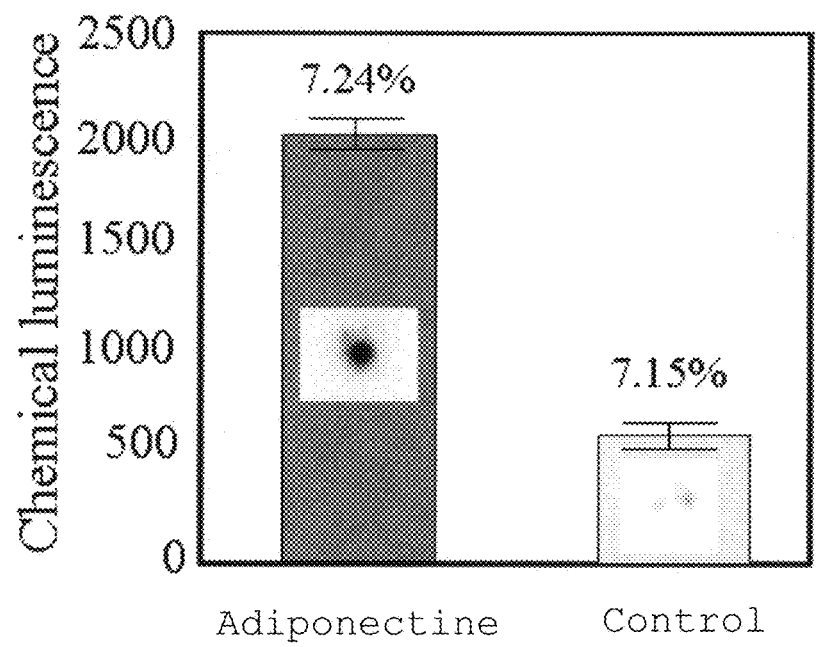
FIG. 13 is a graph showing results of an assay in a device of the present invention in which the primary antibody and the secondary antibody are fixed to the micro flow path in advance.

The results confirmed that the assay device of Example 3 also showed a clear difference between the case where the antibody was fixed and the control with regard to the antibody response with the liquid sample (FIG. 13). By using this method, unlike in Example 2, it is not necessary to perform the washing process during the solution exchange, and the detection can be performed in two steps with the flow of the antigen solution and the flow of the luminescence substrate solution, thereby greatly reducing the detection time (the detection time can be reduced from 15 minutes or more (Example 2) to about 5 minutes (Example 3)). Further, since the primary antibody and the secondary antibody were fixed to the micro flow path in advance, it is possible to ensure superior conservation stability for a long period of time before the assay.

Example 4

Assay Using Enzyme

An assay device with the same specifications as the device in Example 2 was used. However, glucose was used as the analyte, and the detection of the analyte was performed using a Glucose Assay Kit (100 assays; Funakoshi Corporation).

The interface for identifying the analyte was produced as follows.

Masking tape (with rubber-based adhesive) was fixed to the first fluid-impervious member 12 at a portion where the enzyme was to be fixed, and a 4% Block Ace solution (phosphate buffer having a pH of 7.4) was applied. The solution was dried by being left unattended for an hour; then, the masking tape was peeled off. 1% trehalose was mixed with the glucose-enzyme mixed solution contained in the kit. A 1-μl droplet of the mixture was disposed in the portion from which the masking tape has been removed, and was left unattended for an hour, thereby fixing the enzyme to the first fluid-impervious member 12. The amount of the enzyme and the concentration of the trehalose can vary depending on the type of the enzyme and the size of the micro flow path 76.

Thereafter, 3% trehalose was mixed with the coloring reagent prepared by using the method recommended for the kit, and the mixture was applied on Block Ace placed upstream of (proximal to) the portion where the enzyme was fixed, and left unattended for an hour, thereby fixing the coloring reagent to the first fluid-impervious member 12.

Figure 14:
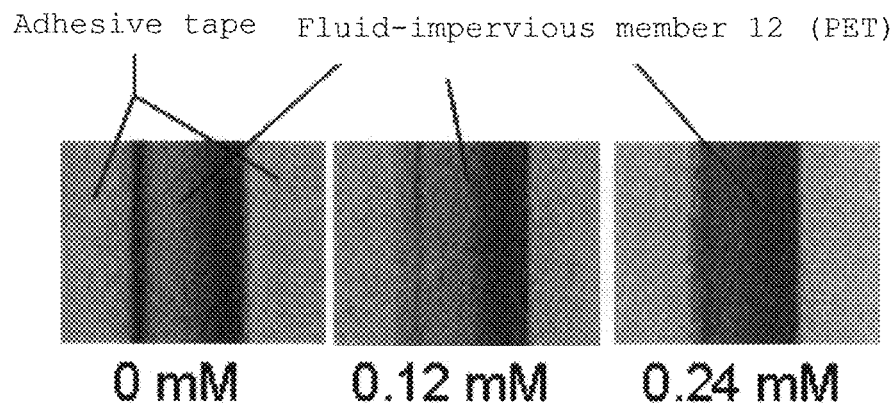
FIG. 14 is a graph showing results of an assay in another device of the present invention using an enzyme.

Next, 5 µl of a test liquid (0 mM, 0.12 mM, or 0.24 mM glucose) was supplied to the assay device, and glucose detection was performed according to the colorimetric method (570 nm). The results showed that the color exhibition was not observed in the control where the glucose (substrate) concentration was 0 mM, and that color change to pale pink and to deep pink were observed in the 0.12 mM glucose solution and the 0.24 mM glucose solution, respectively (FIG. 14).

Example 5

Figure 15:
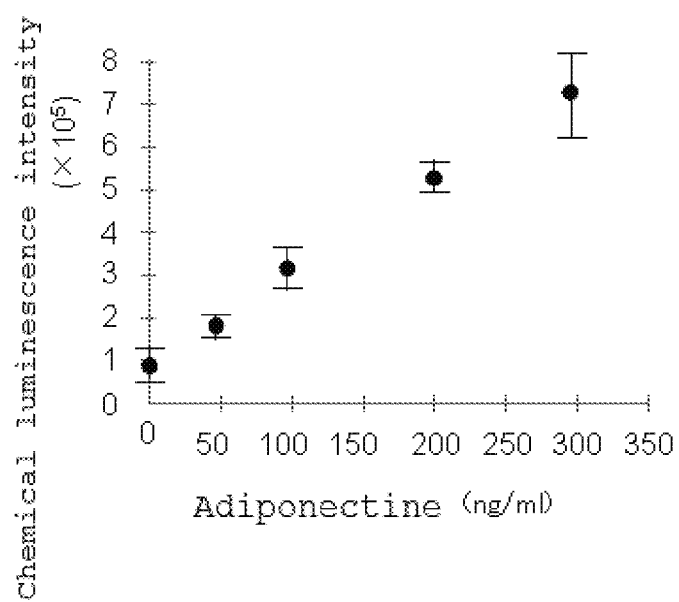
FIG. 15 is a graph showing a relationship between adiponectin concentration and chemical luminescence intensity.

Analysis of Correlation Between Concentration of Analyte and Luminescence Intensity The assay was performed in the assay device under the same conditions as in Example 2 except that the concentration of adiponectin as the analyte was changed to 0 ng/ml, 50 ng/ml, 100 ng/ml, 200 ng/ml, and 300 ng/ml, thereby finding the relationship between the concentration of the analyte and the chemical luminescence intensity. The results showed that the concentration of adiponectin and the luminescence intensity were positively correlated (FIG. 15), and that the assay device of the present invention enables highly accurate detection of the analyte and therefore can be used for the quantitative analysis of unknown analyte concentration.

INDUSTRIAL APPLICABILITY

The assay device of the present invention measures a liquid sample in a micro flow path that is provided as a space, thereby versatilely and securely increasing sensitivity and accuracy in the measurement. The assay device of the present invention is thus useful.

REFERENCE NUMERALS

10: Microfluid device as assay device
12: First fluid-impervious member
18: Hole
20: Second fluid-impervious member
26: Adhesive tape as interposing member
36, 38: Laterally extending portion
50: Cover member as first casing
51: Base member as second casing
67: Plasma separation paper
73: Flow path
74: Assay region
76: Micro flow path
78: First end portion of micro flow path
80: Second end portion of micro flow path
82: Space
42: Development paper
44: Absorbent paper as porous medium
94: Width enlargement portion

The invention claimed is:

1. An assay device comprising:
   a first fluid-impervious member;
   a second fluid-impervious member;
   an interposing member disposed between the first fluid-impervious member and the second fluid-impervious member;
   a micro flow path having a distal end portion and being defined by the first fluid-impervious member, the second fluid-impervious member and the interposing member;
   a porous medium provided near the distal end portion of the micro flow path; and
   a space provided between the micro flow path and the porous medium,
   wherein the porous medium is held between the first fluid-impervious member and the second fluid-impervious member;
   wherein the first fluid-impervious member and the second fluid-impervious member are separate from each other;
   wherein the micro flow path and the space are disposed between the first fluid-impervious member and the second fluid-impervious member; and
   wherein the first fluid-impervious member, the interposing member and the second fluid-impervious member are stacked on each other.

2. The assay device according to claim 1, wherein the cross-sectional area of the space is greater than the cross-sectional area of the micro flow path.

3. The assay device according to claim 1, wherein the volume of the space is not less than 0.001 µl and not more than 10,000 µl, and the capacity ratio of the space to the micro flow path is not less than 0.01.

4. The assay device according to claim 1,
   wherein the fluid comprises a first liquid and a second liquid;
   wherein the device is configured such that
      the first liquid may flow from the micro flow path into the space so that the first liquid is divided by the space, and a first portion of the first liquid stays inside the micro flow path while a second portion of the first liquid is absorbed to the porous medium; and then,
      the second liquid may flow into the micro flow path such that the second liquid pushes the first portion of the first liquid, staying in the micro flow path, to the porous medium.

5. The assay device according to claim 1, wherein the assay device is either structured such that:
   (i) the width of the space is greater than the width of the micro flow path, the height of the space is equal to or greater than the height of the micro flow path, and the ratio of the distance between the micro flow path and the porous medium to the width of the micro flow path is 0.5 to 5; or
   (ii) the width of the micro flow path is equal to the width of the space, the height of the space is greater than the height of the micro flow path, and the ratio of the distance between the micro flow path and the porous medium to the width of the micro flow path is 0.5 to 5; or
   (iii) in a plan view, the space is configured to be enlarged in a tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or (iv) in a plan view, the space is configured with its sides enlarged in a substantially arc-like tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or (v) in a plan view, the space has a first portion that extends from the distal end portion of the micro flow path and is curved toward a longitudinal axis that passes through the width-wise center of the micro flow path, and a second portion that is, in contrast to the first portion, curved toward the outside of the assay device via an inflexion point and is connected to the space for storing the porous medium; the width of the lateral sides of the space is enlarged from the distal end portion of the micro flow path toward the space for storing the porous medium, and the ratio of the distance between the micro flow path and the porous medium to the width of the micro flow path is 1 to 5.

6. The assay device according to claim 1, further comprising a second porous medium in a fluid introduction portion of the micro flow path.

7. The assay device according to claim 6, further comprising plasma separation paper above the second porous medium.

8. The assay device according to claim 6, wherein the micro flow path and the space are treated to be hydrophilic, and the first porous medium and the second porous medium are hydrophilic.

9. The assay device according to claim 1,
wherein the porous medium is a first porous medium,
wherein the device further comprises a second porous medium, and
wherein the second porous medium is held between the first fluid-impervious member and the second fluid-impervious member.

10. The assay device according to claim 9, wherein each surface of the first and second fluid-impervious members is made of a transparent sheet or film.

11. The assay device according to claim 6, further comprising an assay reagent in the micro flow path between the fluid introduction portion and the space.

12. The assay device according to claim 2, wherein the assay device is either structured such that:
  (i) the width of the space is greater than the width of the micro flow path, the height of the space is equal to or greater than the height of the micro flow path, and the ratio of the distance between the micro flow path and the porous medium to the width of the micro flow path is 0.5 to 5; or
  (ii) the width of the micro flow path is equal to the width of the space, the height of the space is greater than the height of the micro flow path, and the ratio of the distance between the micro flow path and the porous medium to the width of the micro flow path is 0.5 to 5; or
  (iii) in a plan view, the space is configured to be enlarged in a tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or
  (iv) in a plan view, the space is configured with its sides enlarged in a substantially arc-like tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or
  (v) in a plan view, the space has a first portion that extends from the distal end portion of the micro flow path and is curved toward a longitudinal axis that passes through the width-wise center of the micro flow path, and a second portion that is, in contrast to the first portion, curved toward the outside of the assay device via an inflexion point and is connected to the space for storing the porous medium; the width of the lateral sides of the space is enlarged from the distal end portion of the micro flow path toward the space for storing the porous medium, and the ratio of the distance between the micro flow path and the porous medium to the width of the micro flow path is 1 to 5.

13. The assay device according to claim 3, wherein the assay device is either structured such that:
  (i) the width of the space is greater than the width of the micro flow path, the height of the space is equal to or greater than the height of the micro flow path, and the ratio of the distance between the micro flow path and the porous medium to the width of the micro flow path is 0.5 to 5; or
  (ii) the width of the micro flow path is equal to the width of the space, the height of the space is greater than the height of the micro flow path, and the ratio of the distance between the micro flow path and the porous medium to the width of the micro flow path is 0.5 to 5; or
  (iii) in a plan view, the space is configured to be enlarged in a tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or
  (iv) in a plan view, the space is configured with its sides enlarged in a substantially arc-like tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or
  (v) in a plan view, the space has a first portion that extends from the distal end portion of the micro flow path and is curved toward a longitudinal axis that passes through the width-wise center of the micro flow path, and a second portion that is, in contrast to the first portion, curved toward the outside of the assay device via an inflexion point and is connected to the space for storing the porous medium; the width of the lateral sides of the space is enlarged from the distal end portion of the micro flow path toward the space for storing the porous medium, and the ratio of the distance between the micro flow path and the porous medium to the width of the micro flow path is 1 to 5.

14. The assay device according to claim 4, wherein the assay device is either structured such that:

(i) the width of the space is greater than the width of the micro flow path, the height of the space is equal to or greater than the height of the micro flow path, and the ratio of the distance between the micro flow path and the porous medium to the width of the micro flow path is 0.5 to 5; or (ii) the width of the micro flow path is equal to the width of the space, the height of the space is greater than the height of the micro flow path, and the ratio of the distance between the micro flow path and the porous medium to the width of the micro flow path is 0.5 to 5; or (iii) in a plan view, the space is configured to be enlarged in a tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or (iv) in a plan view, the space is configured with its sides enlarged in a substantially arc-like tapered shape from the distal end portion of the micro flow path in both directions of the width-wise direction so that the space is connected to the space for storing the porous medium at the end of the taper, and the ratio of the distance between the micro flow path and the porous medium to the width of the micro flow path is 1 to 5; or (v) in a plan view, the space has a first portion that extends from the distal end portion of the micro flow path and is curved toward a longitudinal axis that passes through the width-wise center of the micro flow path, and a second portion that is, in contrast to the first portion, curved toward the outside of the assay device via an inflexion point and is connected to the space for storing the porous medium; the width of the lateral sides of the space is enlarged from the distal end portion of the micro flow path toward the space for storing the porous medium, and the ratio of the distance between the micro flow path and the porous medium to the width of the micro flow path is 1 to 5.

15. The assay device according to claim 1, wherein at least a portion of the first fluid-impervious member extends in parallel to at least a portion of the second fluid-impervious member.

16. The assay device according to claim 1, wherein the device is configured such that, after a fluid moved along the micro flow path based on a lateral flow is brought into contact with the porous medium beyond the space and is absorbed to the porous medium, the fluid is divided by the space so that some of the fluid stays in the micro flow path.

* * * * *